United States Patent [19]

Durante et al.

[11] Patent Number: 5,345,011
[45] Date of Patent: Sep. 6, 1994

[54] NEW MANGANESE CATALYST FOR LIGHT ALKANE OXIDATION

[75] Inventors: Vincent A. Durante, West Chester; James E. Lyons, Wallingford, both of Pa.; Darrell W. Walker, Visalia, Calif.; Bonita K. Marcus, Radnor, Pa.

[73] Assignee: Sun Company, Inc. (R&M), Philadelphia, Pa.

[21] Appl. No.: 124,087

[22] Filed: Sep. 20, 1993

[51] Int. Cl.$^5$ .................. C07C 27/00; C07C 29/50; C07C 31/04; C07C 31/08
[52] U.S. Cl. .................. 568/910; 568/469.9; 568/475; 568/482; 568/910.5
[58] Field of Search .................. 568/910, 910.5, 469.9, 568/482, 475

[56] References Cited

U.S. PATENT DOCUMENTS

| | | |
|---|---|---|
| 4,567,029 | 1/1986 | Wilson et al. |
| 4,803,187 | 2/1989 | Lyons et al. ............ 568/910 |
| 4,864,041 | 9/1989 | Hill .................... 568/910 |
| 4,918,249 | 4/1990 | Durante et al. |
| 4,929,576 | 5/1990 | Tsao et al. |
| 5,012,029 | 4/1991 | Han et al. ............. 568/910 |
| 5,015,798 | 5/1991 | Han et al. |
| 5,068,485 | 11/1991 | Iton et al. |
| 5,132,472 | 7/1992 | Durante et al. |

FOREIGN PATENT DOCUMENTS 1244001 8/1971 United Kingdom .

OTHER PUBLICATIONS

Eusuf et al., "Oxidation of Methane to Methanol; I. Catalysis by Chromium Trioxide Supported on Pumice Stone", Sci. Res. (Dacca) (1969) 6(1–2) 17.

Eusuf et al. "Oxidation of Methane to Methanol; Part II" Bangl. J. Sci. & Ind. Res. (1975) 10 (1–2), 135–141.

*Primary Examiner*—Joseph E. Evans
*Attorney, Agent, or Firm*—Stephen T. Falk; Q. Todd Dickinson

[57] ABSTRACT

Aluminophosphates containing manganese in the structural framework are employed for the oxidation of alkanes, for example the vapor phase oxidation of methane to methanol.

9 Claims, No Drawings

NEW MANGANESE CATALYST FOR LIGHT ALKANE OXIDATION

The government of the United States of America has rights in this invention pursuant to Cooperative Agreement No. DE-FC21-90MC2609 awarded by the U.S. Department of Energy.

FIELD OF THE INVENTION

This invention relates to a method for the direct oxidation of light alkanes to form the corresponding alcohols; in particular, the direct catalytic oxidation of methane to methanol. The catalyst found to be useful in the method of this invention comprises a manganese-substituted aluminophosphate composition.

BACKGROUND OF THE ART

The ability to directly convert methane to methanol in economically satisfactory yields is an important goal of the oil and gas industry. Methane is an abundant material found world-wide, particularly in the form of natural gas. As a gas, it is difficult and costly to transport. Conversion to the liquid methanol allows for safer, more efficient transportation. In addition, methanol is a valuable commercial feedstock, an important ingredient in the production of reformulated motor fuels, and an environmentally compatible fuel in itself.

The conventional method for the catalytic conversion of methane to methanol involves a first reaction with water (steam reforming) to produce synthesis gas, which is a mixture of carbon monoxide and hydrogen, followed by catalytic conversion of the synthesis gas to methanol. A direct, one-step oxidation of methane to methanol would be simpler, and economically and environmentally preferable.

Several catalytic and non-catalytic approaches to directly converting methane to methanol are known in the art. Among these are the following catalytic processes:

United Kingdom Pat. No. 1,244,001 discloses the oxidation of methane to methanol over a catalyst consisting of $(Mo_2O_3) \cdot Fe_2O_3$ on silica/alumina (25% $Al_2O_3$/75% $SiO_2$), sintered to 0.1 g/cm$^2$ at 1000° C., with 65% selectivity (moles methanol/moles product ×100) at 2.1% conversion. The temperature disclosed is 439° C. and the pressure 52 atmospheres. Temperatures, pressures and space rates in the process disclosed in this patent are 300°–550° C.; 5–150 atmospheres; and 20,000–50,000 hr$^{-1}$, respectively.

Eusuf, Sci. Res., Dacca (1969) Vol VI, Nos. 1,2, p.16, discloses the oxidation of methane to methanol over $CrO_3$/pumice. The reported results indicated 12% selectivity at 11% $O_2$ conversion. The reported 8.9% methane conversion is noted to most likely be an error as indicated by the reported carbon/oxygen balance. The actual conversion rate may have been far lower.

Further results on the chlorine-promoted oxidation of methane to methanol over $CrO_3$/pumice were reported in Eusuf, Bangl. J. Sci. Ind. Res. (1975) Vol. 10, Nos 1-2, pp. 135–141 ("Eusuf II"). Eusuf II discloses methane conversion as high as 7.3%, with yields of methanol on input methane basis as high as 46.4%. These results were observed at a temperature of 430° C., pressure at 1.5 atmospheres, and a contact time of 1.5 seconds. The reaction was run in the presence of $Cl_2$ at a volumetric ratio of 0.10, $Cl_2:CH_4$, indicating that there was more chlorine gas present than the amount of methane converted in the reaction.

Few, if any, catalysts currently exist, however, which will promote the direct oxidation of methane to methanol in commercially acceptable yield and selectivity. Durante et al, U.S. Pat. No. 4,918,249, assigned to Sun Company, Inc. (R&M), disclose oxidation of methane to methanol in 70% selectivity at 90% oxygen conversion over an iron framework substituted sodalite catalyst at temperatures around 415° C.

Han et al., U.S. Pat. No. 5,015,798, disclose methane conversion over aluminosilicate zeolite catalyst. Using ZSM-5 zeolite as catalyst, Han et al. disclose methane oxidation to methanol with 5.2% methane conversion and 16.7% methanol selectivity at 450° C. and 960 psig.

Most catalysts which contain oxidation-active transition metals do not produce significant amounts of methanol as oxidation product, but rather tend to combust methane to give carbon oxides and water at the elevated temperatures necessary for oxidation to occur. A catalyst which can oxidize methane to methanol at low temperatures could be very important in producing better selectivities by reducing unwanted carbon oxides.

The process of the present invention involves direct air or oxygen conversion of methane to methanol. No promoter, such as chlorine gas, need be present, which has the added advantage of avoiding the production of chlorocarbon compounds and the creation of a highly corrosive chlorine-containing reaction system.

SUMMARY OF THE INVENTION

The present invention comprises a method for the direct conversion of light alkanes to alcohols, aldehydes and other oxidation products comprising contacting said light alkanes with a catalyst comprising a manganese-substituted aluminophosphate composition.

DETAILED DESCRIPTION OF THE INVENTION

The present invention comprises a method for the direct conversion of light alkanes to alcohols comprising contacting light alkane, in the presence of an oxidant, with a catalyst which comprises a crystalline aluminophosphate (AlPO) structural framework in which a metal is incorporated. Preferably the metal is manganese.

Aluminophosphate-based molecular sieves are crystalline, microporous oxides with alternating trivalent aluminum and pentavalent phosphorus occupying tetrahedral sites that are connected through bridging oxygen atoms. The alumino-phosphates (AlPOs) are corner-linked forming structural frameworks that are analogous to zeolites. Like zeolites, they contain pores in their framework that are molecular in dimension. The overall lattice charge is neutral, and the AlPOs do not have ion exchange capacity or strong acidity.

The AlPOs may have other elements incorporated into their framework (Mn, Fe, Co, Zn, Ga, etc.). Manganese incorporated into the structural framework results in a species designated MnAPO. Incorporation of divalent elements such as manganese generates a negatively charged framework resulting in ion exchange capacity and Bronsted acidity. This, in addition to the high internal surface area and thermal and hydrothermal stability, makes MnAPO a good candidate for use as a commercial catalyst.

According to one embodiment of the present invention, aluminophosphates containing manganese in at least a portion of the structural framework are employed as catalysts. Silicon, gallium, germanium, boron and the like may optionally be present as framework elements of the crystalline structures, so long as aluminum and phosphorus are also present.

The manganese-substituted aluminophosphate compositions (MnAPOs) useful in the present invention comprise between approximately 3 and 13% Mn by weight. The MnAPO catalysts may be prepared according to the technique disclosed in Wilson et al., U.S. Pat. No. 4,567,029, which is incorporated by reference herein. The catalysts used in the process of the invention are particularly suitable for the oxidation of methane to methanol in the vapor phase.

The alkane feedstock for the process of the invention is a hydrocarbon having 1 to 10 carbon atoms. Suitable hydrocarbon feedstocks include aliphatic and cycloaliphatic hydrocarbons, such as methane, ethane, propane, n-butane, isobutane, or mixtures of light alkanes such as natural gas or of alkanes and alkenes in naturally occurring compositions or process streams, hexanes, decanes, toluene, xylene, naphthalene, cyclohexane, methyl cyclohexane, ethyl cyclohexane, tetrahydronaphthalene, decahydronaphthalene and the like. Oxygenates such as alcohols, aldehydes, ketones, esters and the like are prevalent among the products of oxidation of such hydrocarbons.

Olefinic hydrocarbons such as ethylene, propylene and the butylenes may also be oxidized by this process, as may oxygenated hydrocarbon feedstocks. Oxygenated hydrocarbon feedstocks include, for example, methanol, ethanol, isopropyl alcohol, butanols, acetone and higher ketones, aldehydes, cyclohexanol and the like. The products of oxidation are the further oxygenated derivatives of such feedstock, by further oxidation of functional groups or oxidation at additional points in a carbon chain or both.

In one embodiment of the present invention, the oxidation is carried out in a packed bed tubular reactor at temperatures between 300° and 600° C., preferably between 350° and 475° C., and at pressures between 1 and 100 atmospheres, preferably between 30 and 70 atmospheres, with gas hourly space velocities of from 100 to 30,000 h$^{-1}$, preferably 200 to 15,000 h$^{-1}$, and most preferably 200 to 2000 h$^{-1}$ using air or oxygen as the oxidizing gas in combination with the light hydrocarbon. When air is used as the oxidant, hydrocarbon/air ratios of between 0.1 to 10, preferably 0.5 to 5, are effective. When oxygen is used, hydrocarbon/oxygen ratios can be from 0.5 to 50, preferably 5 to 25. Some of these ratios are within explosive limits and care should be taken to operate behind barricades or similarly shielded devices when running in the explosive region. Water may optionally be fed to the reactor with the hydrocarbon-oxidant mixture or after the reactor to capture oxygenated products which are formed. Other reactor configurations (e.g., that described in U.S. Pat. No. 5,132,472, which is incorporated herein by reference) can be used as well which are well known to those skilled in the art.

The following examples illustrate the invention:

EXAMPLE 1

One embodiment of the catalyst useful in the present invention, MnAPO-5, was prepared according to the procedure of U.S. Pat. No. 4,567,029, Example 66. The starting gel ratio was 2.0 diethylethanolamine: 0.167 MnO: 0.917 Al$_2$O$_3$:1 P$_2$O$_5$: 45 H$_2$O. The synthesis was done at 200° C. for one day, quiescently under autogenous pressure. Optical microscopy showed that the synthesis product comprised two distinct morphologies: cubes typical of MnAPO-47 and six-sided rods typical of MnAPO-5. MnAPO-5 has a large pore size (0.8 nm) and is thermally and hydrothermally stable; MnAPO-47 has a smaller pore size (0.43 nm), but is not thermally stable when calcined in air to remove the organic template. X-ray powder diffraction patterns were consistent with those reported by Wilson, U.S. Pat. No. 4,567,029. The material was a mixture with the major phase being MnAPO-5 and minor phase being MnAPO-47.

After calcination of the synthesis product at 600° C. in air for three hours, the X-ray diffraction pattern showed that the MnAPO-47 had collapsed and that the MnAPO-5 remained. Analysis of the calcined material showed the final product to be 5.7 wt % Mn, 17.9 wt % Al, 24.8 wt % P, and 2.45 wt % L.O.I. (loss on ignition).

The sample was bound with a 20% silica binder and sized to 18×35 mesh and was used in the catalytic oxidation of methane and ethane. Oxidation reactions over iron sodalite were run for comparative purposes. Reactions were carried out in a reactor in which the top third was packed with catalyst and the bottom two-thirds was void space. The catalyst was held in place with glass wool plugs. The methane and ethane oxidation results are shown in Table 1 and Table 2, respectively. After use in the reactor, the sample had an x-ray powder pattern consistent with tridymite.

TABLE 1

Methane Oxidation Over MnAPO-5 and Fe$_x$[Fe]SOD$^a$

| Catalyst | Flow ml/min | T °C.$^b$ | Products, mmoles/hr | | | | O$_2$ Conv. % | CH$_4$ Conv. % | CH$_3$OH Sel. % |
|---|---|---|---|---|---|---|---|---|---|
| | | | CH$_3$OH | CH$_2$O | CO | CO$_2$ | | | |
| MnAPO-5 | 55 | 375 | 2.20 | 0.04 | 2.24 | 0.99 | 86 | 4.7 | 40 |
| MnAPO-5 | 98 | 375 | 4.60 | 0.13 | 4.94 | 1.36 | 93 | 5.2 | 42 |
| MnAPO-5 | 377 | 375 | 15.20 | 1.14 | 22.00 | 5.05 | 99 | 5.4 | 35 |
| Fe$_x$[Fe]SOD | 50 | 410 | 2.22 | na | 2.84 | 0.66 | 91 | 5.4 | ≦39 |
| Fe$_x$[Fe]SOD | 92 | 410 | 4.02 | na | 5.32 | 0.96 | 93 | 5.3 | ≦39 |
| Fe$_x$[Fe]SOD | 378 | 410 | 20.96 | na | 19.74 | 3.14 | 90 | 5.5 | ≦48 |
| MnAPO-5 | 55 | 365 | 1.59 | 0.08 | 1.47 | 0.41 | 58 | 3.1 | 45 |
| Fe$_x$[Fe]SOD | 50 | 390 | 0.70 | na | 1.33 | 0.32 | 49 | 2.3 | ≦33 |

$^a$3:1 mixture of methane to air continuously passed over 1.5 cc catalyst top-loaded into a 5 ml heated quartz-lined reactor at 800 psig.

$^b$Applied external temperature (to reactor skin).

TABLE 2

| Catalyst | Flow ml/min | T °C. | $CH_3OH$ | $C_2H_5OH$ | $CH_2O$ | $CH_3CHO$ | Conv. % | Alcohol Sel. % | Liq. Oxyg. Sel. % |
| --- | --- | --- | --- | --- | --- | --- | --- | --- | --- |
| $Fe_x[Fe]SOD$ | 165 | 290 | 33.3 | 16.7 | tr | na | 0.2 | (50.0) | na |
| MnAPO-5 | 92 | 290 | 26.8 | 18.8 | 6.7 | 4.0 | 2.9 | 45.6 | 56.3 |
| $Fe_x[Fe]SOD$ | 161 | 300 | 26.8 | 15.7 | 9.0 | 4.8 | 3.7 | 42.5 | 56.3 |
| MnAPO-5 | 190 | 300 | 36.8 | 21.9 | 11.3 | 5.2 | 3.5 | 58.7 | 75.2 |
| $Fe_x[Fe]SOD$ | 386 | 315 | 20.6 | 6.8 | 15.9 | 4.3 | 3.7 | 27.4 | 47.6 |
| MnAPO-5 | 400 | 300 | 32.6 | 16.3 | 10.9 | 4.5 | 4.0 | 48.9 | 64.3 |

[a]P = 400 psig.; 3:1 mixture of ethane to air.

In this reactor configuration, operating at 375° C., MnAPO-5 was effective for catalytic oxidation of methane to methanol with 35–42% selectivity at about 5% methane conversion. These results compare favorably to those obtained with the iron sodalite catalyst, but at about 35° C. lower temperature.

EXAMPLE 2

Another embodiment of the catalyst useful in the present invention, MnAPO-5[h] with a higher level of manganese, was prepared using the following formation gel ratio:

1.5 Tripropylamine: 0.8 $Al_2O_3$: 1.0 $P_2O_5$: 0.4 MnO: 40 $H_2O$ The synthesis was performed at 170° C. for three days, quiescently under autogenous pressure. X-ray powder diffraction of the material was consistent with the MnAPO-5 pattern listed in U.S. Pat. No. 4,567,029. The sample was calcined in nitrogen at 500° C. for two hours to remove the organic template; the X-ray diffraction showed excellent retention of crystallinity. Analysis of the calcined material showed the product to be 6.4 wt % Mn, 16.7 wt % Al, 20.2 wt % P, 14.1 wt % L.O.I.

The sample was made into a self-supporting mesh and used in the catalytic oxidation of methane. The methane oxidation results are shown in Table 3. The sample after use in the reactor had an x-ray powder pattern consistent with MnAPO-5 with excellent crystallinity.

TABLE 3

| | | Methane Oxidations[a] over MnAPO-5[h] | | | | | | |
| --- | --- | --- | --- | --- | --- | --- | --- | --- |
| Flow ml/min | T °C. | Products, mmoles/hr | | | | $O_2$ Conv. % | $CH_4$ Conv. % | $CH_3OH$ Sel. % |
| | | $CH_3OH$ | $CH_2O$ | CO | $CO_2$ | | | |
| 49 | 375 | 0.73 | 0.05 | 0.75 | 0.85 | 65 | 2.3 | 31 |
| 47 | 385 | 1.36 | 0.05 | 1.1 | 1.5 | 86 | 4.1 | 34 |
| 91 | 395 | 2.88 | 0.20 | 3.8 | 1.8 | 84 | 4.4 | 33 |
| 199 | 395 | 4.16 | 0.49 | 5.4 | 2.8 | 62 | 3.0 | 32 |

[a]P = 800 psig; 3:1 mixture of methane to air; GHSV = 1000 hr$^{-1}$.

EXAMPLE 3

Another embodiment of the catalyst useful in the present invention, MnAPO-11, was prepared according to the procedure of U.S. Pat. No. 4,527,029, Example 75. The starting gel ratio was: 1.0 Diisopropylamine: 0.167 MnO: 0.917 $Al_2O_3$: 1 $P_2O_5$: 40 $H_2O$ The synthesis was performed at 200° C. for three days, quiescently under autogenous pressure. The x-ray diffraction pattern of the material was consistent with that of MnAPO-11. The sample was calcined at 500° C. for one hour in air, and the x-ray diffraction pattern remained consistent with that of MnAPO-11. The MnAPO-11 structure has a 10 ring opening (3.9×9.3 A) and is one dimensional. Analysis of the calcined material showed the final product to be 3.5 wt % Mn, 17.9 wt % Al, 21.4 wt % P, and 12.31 wt % L.O.I.

The sample was bound with 20% silica, meshed and used in the catalytic oxidation of methane. Table 4 compares the catalytic activity of MnAPO-11, MnAPO-5, MnAPO-5[h] and FAPO-11 (an iron aluminophosphate) for the oxidation of methane in air. After use in the reactor, the x-ray powder pattern was consistent with MnAPO-11, but with decreased crystallinity compared to the starting material.

TABLE 4

| | Methane Oxidation Over Framework-Substituted Zeolites[a] | | | | |
| --- | --- | --- | --- | --- | --- |
| Catalyst | T °C. Ext | T °C. Int | $CH_3OH$ Sel. % | $O_2$ Conv. % | $CH_4$ Conv. % |
| Empty Tube | 350 | 351 | — | 6 | ≦0.1 |
| $SiO_2$ | 350 | 350 | 21 | 15 | 0.3 |
| Empty Tube | 365 | 365 | 44 | 19 | 0.9 |
| $SiO_2$ | 365 | 365 | 35 | 22 | 1.1 |
| MnAPO-11 | 365 | 359 | 42 | 48 | 1.9 |
| MnAPO-5 | 365 | — | 45 | 58 | 3.1 |
| Empty Tube | 375 | 378 | 38 | 93 | 4.5 |
| $SiO_2$ | 375 | 375 | 32 | 30 | 1.8 |
| FAPO-11 | 375 | 375 | 46 | 49 | 2.2 |
| MnAPO-5[h] | 375 | — | 31 | 65 | 2.3 |
| MnAPO-11 | 375 | 369 | 45 | 79 | 3.7 |
| MnAPO-5 | 375 | — | 40 | 86 | 4.7 |

[a]P = 800 psig; 3:1 mixture of methane ot air; GHSV = 1000.

EXAMPLE 4

Another embodiment of the catalyst useful in the present invention, MnAPO-44, was prepared according to the procedure, of U.S. Pat. No. 4,567,029, Example 87, with the following modifications: the digestion was done stirred, not quiescently; the scale was three-times the patent scale; and the digestion time was shortened to three days. The starting gel ratio was 1 cyclohexylamine: 0.2 MnO: 0.8 $Al_2O_3$: 1 $P_2O_5$: 50 $H_2O$ The digestion was done at 150° C. in a stirred reactor. X-ray powder diffraction of the dried material was consistent with a mixture of MnAPO-44 and MnAPO-13; H3 was present as an impurity phase.

After calcination of the synthesis product at 500° C. for two hours, the x-ray diffraction pattern showed that the material had collapsed to tridymite, pseudo-boehmite and $AlPO_4$-D. Analysis of the calcined product showed the final product to comprise 23.1 wt % P, 18.0 wt % Al, 8.1 wt % Mn. The catalytic activity of the MnAPO sample for the oxidation of methane is compared in Table 1 with that of alundum (from which no attempt was made to remove iron traces), silica, and an iron sodalite prepared according to Durante et al., U.S. Pat. No. 4,918,249. Results are dependent on reactor configuration. The reactor used in this example was a tube top-filled approximately one-third with catalyst with the bottom two-thirds being void space.

Under the conditions described in Table 5, the MnAPO catalyst showed 51% methanol selectivity at a 4.0% conversion of methane. Under these conditions, MnAPO had comparable activity to active iron sodalite.

TABLE 5

Comparative Catalytic Methane Oxidation[a]

| Catalyst | Products (mmol/hr) | | | $O_2$ Conv. (mole %) | $CH_4$ Conv. (mole %) | $CH_3OH$ Sel (Carbon mole %) |
| --- | --- | --- | --- | --- | --- | --- |
| | CO | $CO_2$ | $CH_3OH$ | | | |
| $\alpha$-$Al_2O_3$ | 2.6 | 0.6 | 1.5 | 18 | 1.2 | 32 |
| $SiO_2$ | 3.6 | 0.8 | 3.0 | 37 | 1.9 | 41 |
| $Fe_x$[Fe]SOD | 6.8 | 1.2 | 7.8 | 65 | 4.0 | 50 |
| MnAPO | 6.7 | 1.2 | 8.2 | 65 | 4.2 | 51 |

[a]A 3:1 mizxture of methane and air (5% $O_2$; 800 psig) was passed over the catalyst (GHSA = 2800 h$^{-1}$, based on total heated reactor volume) at 392° C. Product quantities were determined by a combination of gas chromatography and mass spectral analysis.

What is claimed is:

1. A method for the direct oxidation of light alkanes comprising contacting said light alkane, in the presence of an oxidant, with catalyst comprising manganese and a crystalline aluminophosphate structural framework, wherein at least a portion of said manganese is incorporated in said structural framework.

2. The method as claimed in claim 1, wherein the amount of manganese in said catalyst is in the range of approximately 3 to 13 weight percent.

3. The method as claimed in claim 1, wherein said light alkane comprises methane, ethane, propane, natural gas, or mixtures thereof.

4. The method as claimed in claim 3, wherein said light alkane comprises methane.

5. The method as claimed in claim 1, wherein said oxidant comprises oxygen, air, or mixtures thereof.

6. The method as claimed in claim 1, wherein said oxidation of light alkane is carried out in a reaction zone maintained at a temperature in the range of approximately 200° C. to 450° C.

7. The method as claimed in claim 6, wherein said temperature is in the range of approximately 300° to 400° C.

8. The method as claimed in claim 6, wherein said reaction zone is maintained at a pressure in the range of approximately 400 to 1200 psig.

9. The method as claimed in claim 8, wherein said pressure is approximately 800 psig.

* * * * *